US00PP11697P

United States Patent [19]

Craig et al.

[11] Patent Number: Plant 11,697

[45] Date of Patent: Dec. 19, 2000

[54] REGAL PELARGONIUM PLANT NAMED 'DANDY'

[75] Inventors: Richard Craig, State College, Pa.; David G. Clark, Gainesville, Fla.

[73] Assignee: Penn State Research Foundation, University Park, Pa.

[21] Appl. No.: 09/164,540

[22] Filed: Sep. 30, 1998

[51] Int. Cl.[7] ..... A01H 5/00

[52] U.S. Cl. ..... Plt./331

[58] Field of Search ..... Plt./331

[56] References Cited

U.S. PATENT DOCUMENTS

P.P. 6,080 1/1988 Kirmann ..... Plt./331

P.P. 7,387 12/1990 Craig et al. ..... Plt./331

P.P. 10,445 6/1998 Lemon ..... Plt./331

*Primary Examiner*—Bruce R. Campell

*Assistant Examiner*—Wendy A Baker

*Attorney, Agent, or Firm*—Webb Ziesenheim Logsdon Orkin & Hanson, P.C.

[57] ABSTRACT

A new and distinct regal geranium plant with striking rose pink colored flowers having some petals accented by a very deep burgundy middle shading to bright pink with salmon highlights above medium green foliage. The new cultivar has improved cutting production, rooting speed, crop time and flower quantity over 'Majestic' and 'Grand Slam'.

1 Drawing Sheet

BACKGROUND OF THE INVENTION

This discovery relates to a new and distinct cultivar of geranium identified by the name of 'Dandy', Breeder No. 93-30-16 and Oglevee, Ltd. No. 19. The seedling of the present cultivar was the offspring of parent plants, identified by Breeder Nos. 90-70-20 and 90-93-20, which are maintained proprietary by the breeder, in a selective breeding program conducted at The Pennsylvania State University, Department of Horticulture, University Park, Pa. The purpose of the breeding program was to create new regal geranium genotypes with clear, bright color flowers, excellent propagation characteristics, compact growth habit, predictable and consistent flowering response and good post-harvest quality. The new cultivar was discovered at The Pennsylvania State University, University Park, Pa. and was first asexually reproduced by cuttings on Oct. 3, 1994. It has been found to retain its distinctive characteristics through successive generations.

The new cultivar, when grown in a glass greenhouse in Connellsville, Pa. using full light, 60° F. night temperature, 68° F. day temperature and grown in a soilless media with constant fertilizer at 150–200 ppm nitrogen and potassium, has a response time from a rooted cutting to a flowering plant in a 6 inch pot of fourteen weeks. Rooted cuttings potted Oct. 15, 1997 flowered on Feb. 9, 1998.

DESCRIPTION OF THE DRAWING

The accompanying photographic drawing illustrates the new cultivar, with the color being as nearly true as is possible with color illustrations of this type. The colors described in the specification are seen when viewing the plant in person, and the photographic drawing illustrates the specified colors as best as possible.

DESCRIPTION OF THE PLANT

The following detailed descriptions set forth the characteristics of the new cultivar. The data which define these characteristics were collected from asexual reproductions carried out at Oglevee, Ltd., 152 Oglevee Lane, Connellsville, Pa. 15425. The color readings on a plant grown in a 5 inch pot were taken indoors under 200–220 foot candles of cool white fluorescent light. Color references are primarily to The R.H.S. Colour Chart of The Royal Horticultural Society of London.

THE PLANT

Classification:
- *Botanical.*—*Pelargonium×domesticum.*
- *Varietal.*—Regal geranium named 'Dandy'.

Form: Upright mound.
Height: 22.0–23.5 cm.
Growth: Medium plant habit with basal branching.
Strength: No artificial support needed.
Rooting speed: Cuttings produce 3 to 5 roots visible to outside of artificial growing media in 14 to 21 days.
Foliage: Stalked leaf attachment.
Leaves:
- *Size.*—8.0–9.0 cm wide, 2.5 cm long.
- *Shape.*—Depressed ovate; truncate base.
- *Margin.*—Serrately lobed.
- *Texture.*—Rough, pubescent.
- *Color.*—Upper Surface: Green Group 137C. Bottom Surface: Green Group 137B. Zone: None.
- *Ribs and veins.*—Venation: Palmate. Color: Green Group 138D.

Petioles:
- *Length.*—6.0–9.0 cm.
- *Color.*—Yellow-Green Group 144A.

Stem:
- *Color.*—Yellow-Green Group 144A.
- *Internode length.*—1.5–2.0 cm.

THE BUD

Shape:
- *Overall.*—Elliptical cluster when no color showing.
- *Individual Buds.*—Ellipitcal or oval when no color showing.

Size: 4.0–5.0 cm wide, 2.5–3.5 cm long.
Number of buds per cluster when color showing: 9 to 15.

INFLORESCENCE

Blooming habit: Large florets forming a full, continuous flower head; blooms 24.0–26.5 cm above the media surface; 9 to 15 florets per cluster when fully opened.

Borne: Umbel, florets on pedicel, pedicel on peduncle.

Closed florets:

*Bud size.*—2.0–2.5 cm long.

Open florets:

*Form.*—Slightly cupped.

*Size of fully open bloom.*—Umbels: 7.0–8.0 cm across. Florets: 3.0–4.5 cm across: 4.0–4.5 cm long.

*Color.*—Top: Upper two petals have white base with very prominent middle of Greyed-Purple Group 187A shading to Red Group 53A and then to Red Group 53D at the edge. The white base is not readily apparent in the photographic illustration. Veining is Greyed-Purple Group 187A shading to Red-Purple Group 71A. Lower three petals have a base of Red-Purple Group 68D deepening to Red-Purple Group 58C. Bottom: Upper two petals have an overall color of Red Group 53D with eye and veining showing through. Lower three petals have an overall color of Red-Purple Group 58D with veining and eye showing through slightly. Eye: All three lower petals have eyes, some are much less pronounced than others. Eye is Red Group 53A at darkest to Red Group 53C being the lightest. Veining is Red Group 54A.

*Petals.*—5–6 in number.

Texture and appearance: Highly reflective; appears from a distance as striking rose pink flowers with some petals being accented by a very deep burgundy middle shading to bright pink with salmon highlights above medium green foliage.

*Petaloids.*—None.

Pedicel:

*Length.*—2.5–3.0 cm.

*Color.*—Yellow-Green Group 144A.

Peduncle:

*Length.*—8.5–9.0 cm.

*Color.*—Yellow-Green Group 144A.

Disease resistance: No unusual susceptibility to diseases or pests has been noted to date.

Lasting quality: Overall plant bloom lasts 14 to 21 days when brought into the home as an indoor flowering pot plant.

REPRODUCTIVE ORGANS

Stamens:

*Anthers.*—3.0–4.0 mm long.

*Filaments.*—Length: 1.4–1.7 cm. Color: Red-Purple Group 68D.

*Pollen color.*—Golden orange.

Pistils:

*Number.*—1.

*Length.*—2.0–2.2 cm.

*Stigma color.*—Red-Purple Group 59A.

*Style.*—1.1–1.2 cm long.

*Ovaries.*—Pale green; pubescent; superior; 5.0–6.0 mm long.

Fruit: None observed.

GENERAL CHARACTERISTICS

Cutting produciton, rooting speed, crop time and flower quantity are all improved over 'Majestic' U.S. Plant Pat. No. 7,387 and 'Grand Slam' (unpatented). Consistent early flower response time and longer keeping quality are also good characteristics of this new cultivar. In particular, 'Dandy' is earlier to flower than 'Majestic' and 'Grand Slam' by 2 weeks and 4 weeks, respectively. 'Dandy' remains in flower in the home under low light for 14 to 21 days, whereas 'Majestic' lasts 12 to 16 days and 'Grand Slam' lasts 10 to 12 days. 'Dandy' has been trialed during the winters and springs of 1996–1997 and 1997–1998 and has proven to be reliable and consistent.

We claim:

1. A new and distinct cultivar of regal geranium plant named 'Dandy' as described and illustrated herein.

* * * * *

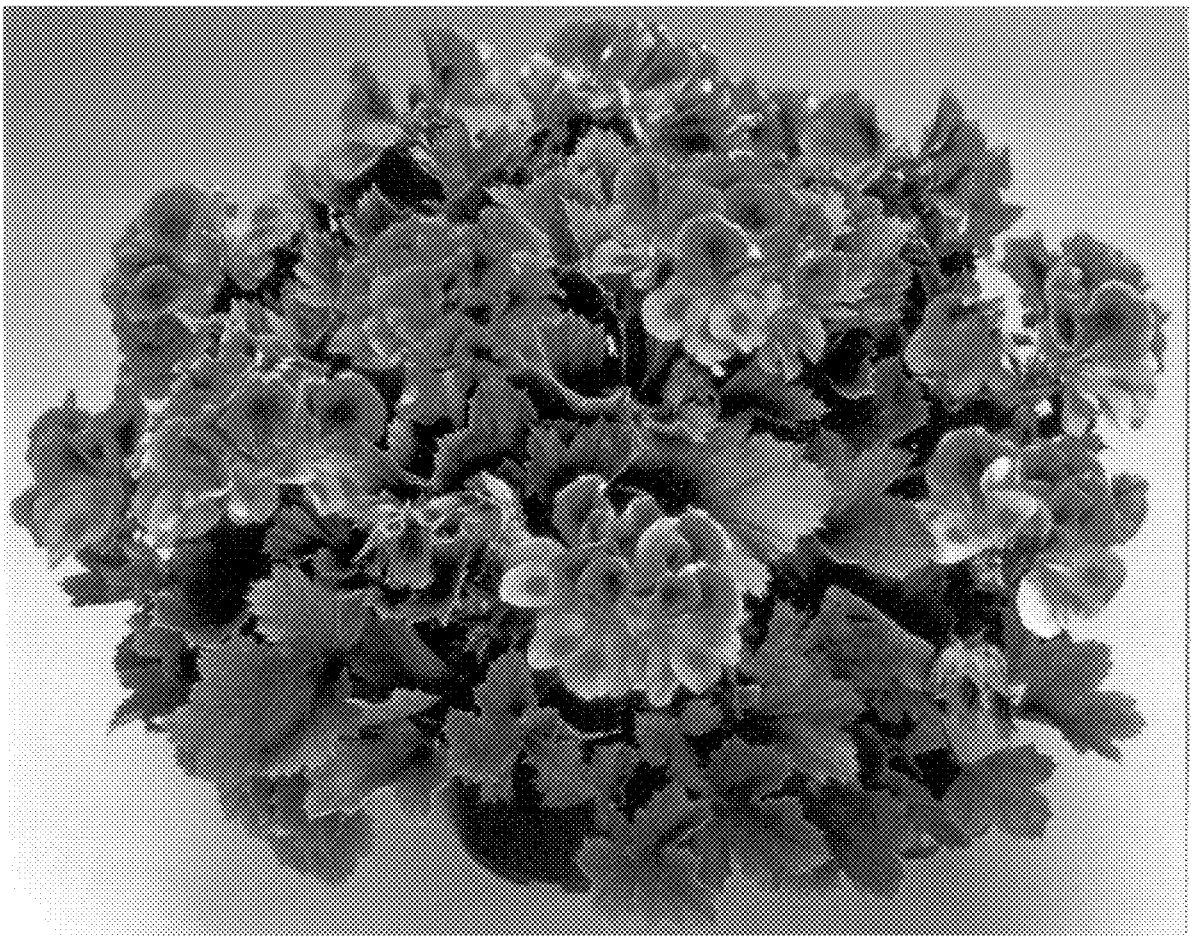

UNITED STATES PATENT AND TRADEMARK OFFICE

CERTIFICATE OF CORRECTION

PATENT NO. : PP 11,697
DATED : December 19, 2000
INVENTOR(S) : Richard Craig et al.

It is certified that error appears in the above-identified patent and that said Letters Patent is hereby corrected as shown below:

Title page,
Column 1, line 2, insert
-- This invention was made with government support under USDA Hatch Act Project Nos. PEN03030 and PEN03393. --.

Signed and Sealed this

Fifteenth Day of November, 2005

JON W. DUDAS
*Director of the United States Patent and Trademark Office*